United States Patent

Newman, Jr. et al.

(10) Patent No.: US 6,794,484 B2
(45) Date of Patent: Sep. 21, 2004

(54) CRYSTALLIZABLE POLYLACTONE COPOLYMERS PREPARED FROM MONO- AND DI-FUNCTIONAL POLYMERIZATION INITIATORS

(75) Inventors: Hugh D. Newman, Jr., Chester, NJ (US); Sasa Andjelic, New York, NY (US); Brian M. Kelly, Bedminster, NJ (US); Dennis D. Jamiolkowski, Long Valley, NJ (US); Rao S. Bezwada, Whitehouse Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/185,053

(22) Filed: Jun. 28, 2002

(65) Prior Publication Data

US 2004/0002580 A1 Jan. 1, 2004

(51) Int. Cl.$^7$ .................. C08G 69/08; C08G 73/10; A61B 17/08
(52) U.S. Cl. .................. 528/354; 528/355; 528/358; 528/359; 528/361; 525/411; 525/413; 525/415; 606/151; 606/224; 606/228; 606/230; 606/231
(58) Field of Search .................. 528/354, 355, 528/359, 361; 525/411, 413, 415; 606/151, 224, 228, 230, 231

(56) References Cited

U.S. PATENT DOCUMENTS

| | | | | |
|---|---|---|---|---|
| 4,653,497 A | * | 3/1987 | Bezwada et al. | 606/230 |
| 4,744,365 A | * | 5/1988 | Kaplan et al. | 606/230 |
| 4,838,267 A | * | 6/1989 | Jamiolkowski et al. | 606/224 |
| 5,007,923 A | * | 4/1991 | Bezwada et al. | 606/231 |
| 5,076,807 A | * | 12/1991 | Bezwada et al. | 606/230 |
| 5,080,665 A | * | 1/1992 | Jarrett et al. | 606/219 |
| 5,133,739 A | * | 7/1992 | Bezwada et al. | 606/230 |
| 5,376,102 A | * | 12/1994 | Jarrett et al. | 525/415 |
| 5,409,499 A | * | 4/1995 | Yi | 606/151 |
| 5,470,340 A | * | 11/1995 | Bezwada et al. | 606/231 |
| 5,633,343 A | * | 5/1997 | Bezwada et al. | 528/361 |
| 5,713,920 A | * | 2/1998 | Bezwada et al. | 606/230 |
| 5,869,597 A | * | 2/1999 | Newman et al. | 528/348 |
| 5,951,997 A | | 9/1999 | Bezwada et al. | 528/354 |
| 6,130,271 A | * | 10/2000 | Jarrett et al. | 523/113 |
| 6,462,169 B1 | * | 10/2002 | Shalaby | 528/354 |
| 2003/0120029 A1 | * | 6/2003 | Shalaby et al. | 528/310 |

FOREIGN PATENT DOCUMENTS

| | | |
|---|---|---|
| EP | 0908142 A2 | 4/1999 |
| WO | 0908482 A1 | 4/1999 |
| WO | WO 01/40348 A2 | 6/2001 |

OTHER PUBLICATIONS

Copy of European Search Report.

* cited by examiner

*Primary Examiner*—P. Hampton Hightower (57) ABSTRACT

The present invention is directed to absorbable polylactone copolymers prepared in part from about 2 to about 80 mole percent glycolide, utilizing a combination of a monofunctional polymerization initiator and a di-functional polymerization initiator, to achieve rates of crystallization of the copolymer of at least about 2 times faster than the rate of crystallization of a copolymer made by a similar process utilizing either the mono-functional or the di-functional polymerization initiator alone. Medical devices containing such copolymers are also disclosed.

14 Claims, 5 Drawing Sheets

CRYSTALLIZABLE POLYLACTONE COPOLYMERS PREPARED FROM MONO- AND DI-FUNCTIONAL POLYMERIZATION INITIATORS

FIELD OF THE INVENTION

The present invention relates to methods of making absorbable polylactone copolymers suitable for use in implantable medical devices, which methods include the use of both mono- and di-functional polymerization initiators, otherwise known as molecular weight control agents, to polymers prepared by such methods and to medical devices prepared from such polymers.

BACKGROUND OF THE INVENTION

Homopolymers and copolymers of p-dioxanone (PDO) are known for use in the medical device and pharmaceutical fields due to their low toxicity, softness and flexibility. Poly(p-dioxanone) (PDS) homopolymer in particular has been suggested as an absorbable polymer for use in synthetic surgical devices. By the early 1980's the PDS homopolymer was used by surgeons in the form of a monofilament surgical suture. Since that time, many p-dioxanone copolymers have been described for use in such devices. Surgical monofilament sutures based on a copolymer prepared from trimethylene carbonate (TMC), glycolide (GLY) and p-dioxanone (PDO) monomer currently are available for use. PDO based polymeric materials also can be injection molded into a number of non-filamentous surgical devices such as surgical clips and fasteners for use in, e.g. meniscal repair. These surgical articles take full advantage of the general toughness exhibited by this family of homopolymers and copolymers known heretofore.

Segmental block copolymers composed of p-dioxanone and glycolide (at a molar ratio of PDO:GLY of approximately 90:10) were thought to be polymers potentially suitable for use as a "soft" monofilament suture having a break strength retention (BSR) profile similar to Vicryl® sutures, available from Ethicon, Inc. However, these copolymers were found to crystallize relatively slowly upon cooling from the melt, making the fiber manufacturing processes more difficult and challenging, and thus hampering the conversion of such polymers to "soft" monofilament sutures. It would be advantageous, then, to determine polymerization process parameters necessary to produce such polymers having properties suitable for conversion to "soft" monofilament sutures, as well as other implantable medical devices. The present invention provides such processes, polymers made by such processes and having unique properties, and medical devices made from such polymers.

SUMMARY OF THE INVENTION

The present invention is directed to a polymerization process for making absorbable polylactone copolymers, wherein from about 2 to about 80 mole percent of a first lactone monomer comprising glycolide and about 98 to about 20 mole percent of a second lactone monomer other than glycolide are contacted with a monofunctional polymerization initiator and a di-functional polymerization initiator, at a molar ratio of monofunctional to di-functional initiator ranging from 10:90 to 90:10, and the glycolide and second lactone monomers are in the presence of the mono-functional and di-functional polymerization initiators under conditions effective to copolymerize the monomers, thereby providing the absorbable polylactone copolymer. When medical devices are manufactured from certain polymers prepared by such processes, the rate of crystallization during formation of the device is at least about 2 times faster, and preferably greater than about 10 times faster, than the rate of crystallization when a polylactone polymer made by a substantially similar or the same polymerization process, but utilizing either the monofunctional or the di-functional polymerization initiator alone, is used to form the device. Thus, the present invention provides increased crystallization rates as compared to conventional processing, as taken under the same or similar measurement conditions or techniques. The invention also is directed to absorbable polylactone copolymers prepared by processes of the present invention and to medical devices comprising such copolymers.

DETAILED DESCRIPTION OF THE INVENTION

Properties of monofilament fibers produced from polylactone copolymers comprising glycolide copolymerized with a second lactone monomer other than glycolide, including fiber strengths, stiffness and break strength retention, were found to vary depending on whether the polymerization reaction used to prepare the copolymers was initiated with monofunctional initiators or di-functional initiators. It now has been discovered unexpectedly that the use of a combination monofunctional and di-functional polymerization initiators in polymerization processes, e.g. ring-opening polymerization, may provide certain polylactone copolymers that, in turn, provide improved crystallization characteristics during manufacture of certain medical devices manufactured at least in part from such polylactone copolymers.

In order to produce a high molecular weight polymer by a ring-opening polymerization (ROP) in a timely, reproducible and economical fashion, a catalyst usually is combined with a mono- or multi-functional initiator. These initiators are desirably hydroxyl-containing compounds, usually primary alcohols, that can be used to generate linear or branched polymers. If the initiator contains one or two hydroxyl groups, a linear material will result. It is expected that both mono- and di-functional initiators normally will produce linear materials because one chain, without branch points, is produced from each molecule of initiator. If the initiator contains three or more hydroxyls, branched materials are generally formed. Various catalysts for the ring ring-opening polymerization of lactones have been used. They are generally metal based and include the organic titanates and zirconates (as sold by DuPont under the tradename TYZOR) Organotin compounds have found great utility as catalysts for the ring-opening polymerization of lactones for medical applications. Tin catalysts include Sn (IV) compounds such as dibutyltin oxide and Sn (II) compounds such as stannous chloride. Particularly advantageous for use as a catalyst is stannous octoate.

The polymerization is conveniently done in a bulk process, i.e. solventless, although it also may be conducted in solution. The polymerization is usually conducted in the melt, that is, above the melting points of the various monomers making up the feed, as well as above the melting point of the forming polymer. In some special cases, the ring-opening polymerization of certain lactones can be conducted in the solid state, that is, below the melting point of the forming polymer. An example of the later is the homopolymerization of p-dioxanone. Although the total-monomer-to-total-initiator molar ratio can range from about 100:1 to about 10,000:1, the preferred range of the total-monomer-to-total-initiator molar ratio for polymer to be used in extrusion and injection molding processes ranges from about 400:1 to about 2,000:1. This is because the amount of initiator greatly influences the molecular weight of the formed resin. In the absence of side reactions, each initiator molecule ideally generates one polymer chain. The more relative initiator available, the greater the number of chains formed and consequently the lower the molecular weight of the resin formed. In the preferred range of total-monomer-to-total-initiator molar ratio of about 400:1 to about 2,000:1, the molecular weight of the resulting polymer is more suitable for extrusion and injection molding applications.

Cyclic esters, i.e. lactones, that function as suitable monomers can be selected from the group comprising small rings, especially the 5-, 6-, and 7-member rings. Of particular utility are the lactones containing a heteroatom, especially oxygen, adjacent to the α-carbon. Preferred 6-member cyclic esters include glycolide, L(−)-lactide, D(+)-lactide, meso-lactide, and p-dioxanone. A preferred 7-member lactone is ε-caprolactone (epsilon-caprolactone). The characteristics of suitable monomer for the present invention include those that provide reasonable reaction rates under suitable reaction conditions. The polymers that are formed are advantageously biocompatible, making them suitable for the fabrication of medical devices.

One of the characteristic methods for preparation of branched and highly functional aliphatic polyesters might involve hydroxyl functionalities as the pendant groups in a polymer chain. See for instance the work of M. Trollsas, J. L. Hedrick, D. Mecerreyes, Ph. Dubois, R. Jerome, H. Ihre, and A. Hult, in Macromolecules 1998, 31, 2756. These molecules containing a plurality of pendant hydroxyl groups might serve as macroinitiators for the initiation of ring-containing monomers in a subsequent copolymerization step to prepare dendri-graft (comb) molecular structures. Similarly, hydroxyl groups of multifunctional initiators might be fully substituted to produce star-shaped polymers with two, four, five and six arms. See for instance the work of A. Schindler, Y. M. Hibionada, and C. G. Pitt in the Journal of Polymer Science: Polymer Chemistry Edition 1982, 20, 319 as well as the work of C. A. P Joziasse, H. Grablowitz, and A. J. Pennings in Macromol. Chem. Phys. 2000, 201, 107.

Due to their unique molecular architecture, branched compounds exhibit different physiochemical properties compared to their linear counterparts. It is generally recognized that long-branches can decrease viscosity, thus improving processability in some instances, and increase elasticity, while short chain branches predominately affect crystallinity. For instance, F. Tasaka, Y. Ohya, and T. Ouchi (Macromolecules 2001, 34, 5494) graft polymerized l-lactide (LA) in bulk using $Sn(Oct)_2$ in the presence of poly[(Glc-Ser)-LA] having pendant hydroxyl groups as a macroinitiator. Such obtained comb-like polymers showed a substantial reduction in crystallinity compared to the linear poly (L-lactide), PLLA (15–22% vs. 55%). An abrupt decrease in both the glass transition temperature (40–43° C. vs. 65° C.) and the melting point (135–140° C. vs. 167° C.) was also detected. Owing to the lower crystallinity, biological properties are affected as well. In vitro degradation rate of comb-type PLLA was found to be significantly faster than that of linear PLLA.

The rheology of a polymer melt even within one structure or chemistry, as related to processing and fabrication, is affected by many factors such as the molecular weight and molecular weight distribution, the polymer architecture and blending. In particular, long chain branching has a significant contribution. Although limiting the synthesis to linear materials helps to simplify the processing and fabrication issues that would arise because of the contributions that branching would bring to the melt rheology, crystallization concerns speak away from branched materials. Although we do not wish to be limited by scientific theory, branched polymers frequently are more difficult to crystallize when compared to unbranched (linear) materials of the material.

Returning to linear materials, mono- or di-functional initiators, as already alluded to, have found extensive use in producing polymers useful for producing absorbable surgical devices. Diols have been used in ring opening "prepolymerizations" to produce α,ω-dihydroxy-macroinitiators (alpha, omega-dihydroxymacroinitiators) that are then used in a subsequent copolymerization to produce polymers with special sequence distributions. This sequential addition ROP, in which a monomer feed portion is added in a subsequent step, is one method to make so-called segmented block copolyesters. An example is a glycolide/epsilon-caprolactone copolymer that has enjoyed considerable commercial success. See R. S. Bezwada, D. D. Jamiolkowski, et. al., "MONOCRYL™ Suture, a New Ultra-Pliable Absorbable Monofilament Suture" Biomaterials, 16 (15), 1141–1148 (1995).

Within the scope of the present invention is the use of mono- or di-functional initiators in sequential addition ring opening polymerizations in which the monomer feed is added in sequence. That is, portions of the total monomer are allowed to enter the reactor in sequence or in mutiple steps, as opposed to having all the monomer added at once. It is also within the scope of the present invention polymerization processes in which the monomer is indeed added to the reactor in substantially in a single step at the start of the polymerization. In all cases, it should be understood that the monomers employed can be added to the reactor as solids, in the case where the monomers are indeed a solid at room temperature, or as molten liquids. If the reaction is to be conducted in the presence of a solvent, the monomers may be added in solution. It is also within the scope of the present invention polymerization processes in which the initiators are added in sequence or are added independently added as a function of time.

In the absence of transesterification, the molecular weight distributions may be slightly different. For instance, Mw/Mn values of 2 and 1.5 are expected for polymers made with mono- and di-functional initiators, respectively. In the presence of substantial transesterification, a value of two is approached for both types. Likewise, the monomer sequence distribution in copolymerizations may differ slightly as well. In studying the effect of the functionality of the initiator in the sequential addition ROP of lactones, the use of mono- and di-functional alcohols was explored. One would expect the properties of polymers made using a mixture of mono-functional and di-functional initiators to lie between the extremes exhibited by materials based on only mono- or only di-functional initiators. Contrary to such expectation, it was discovered that employing a mixture of mono- and di-functional initiators can produce structures that are unexpectedly different and that have very advantageous properties. They include much more rapid crystallization characteristics, with a resultant impact in processability, and mechanical and biological performance enhancements.

Initiators of lactone ring-opening polymerizations can, under the right conditions, be aliphatic alcohols, phenols, thiols or mercaptans, thiophenols, or amines. Alcohols, of course, possess hydroxyl groups, while thiols possess sulfhydryl groups. The alcohols and amines may be primary, secondary or tertiary and they may be linear or branched. Of particular utility are aliphatic alcohols, especially primary aliphatic alcohols. Of even greater utility are primary aliphatic alcohols of low volatility. Once placed in the reactor, such initiators are not easily lost during vacuum purging cycles, thus allowing much better process control of the resulting polymer's molecular weight. For purposes of the present invention, in determining whether an initiator is classified as a mono- or di-functional initiator, only those functional groups capable of initiating lactone ring-opening polymerization will be considered as an "initiator" functional group. Thus, initiators may have more than one functional group and still be considered to be a mono-functional initiator for purposes of the present invention. For instance, an initiator may simultaneously contain a hydroxyl group and a halide. As the hydroxyl is capable of initiating ring-opening polymerization and a halide is not, such an initiator would be considered monofunctional. Thus for purposes of the present invention, 10-methoxyoctanol ($CH_3OCH_2CH_2CH_2CH_2CH_2CH_2CH_2CH_2OH$) is considered mono-functional, even though it possesses both a hydroxyl group and an ether group.

Preferred monofunctional initiators are $C_4$ or higher primary aliphatic alcohols, especially $C_{10}$ or higher linear primary aliphatic alcohols such as 1-dodecanol. Primary aliphatic monofunctional alcohols include: 1-hexanol, 1-heptanol, 1-octanol, 1-nonanol, 1-decanol, 1-hendecanol, 1-dodecanol (lauryl alcohol), 1-tridecanol, 1-tetradecanol (myristyl alcohol), 1-pentadecanol, 1-hexadecanol (cetyl alcohol), 1-heptadecanol, 1-octadecanol (stearyl alcohol), and branched primary aliphatic monofunctional alcohols such as 10-methyl-1-hendecanol (isolauryl alcohol), 9-methyl-1-hendecanol (anteisolauryl alcohol), 12-methyl-1-tridecanol (isomyristyl alcohol), 11-methyl-1-tridecanol (anteisomyristyl alcohol), 14-methyl-1-pentadecanol (isopalmityl alcohol), 13-methyl-1-pentadecanol (anteisopalmityl alcohol), 16-methyl-1-heptadecanol (isostearyl alcohol), and 15-methyl-1-pentadecanol (anteisostearyl alcohol). Primary aliphatic monofunctional alcohols can be mutibranched in nature such as 2,6,10,14-tetramethyl-1-pentadecaonol ($C_{19}H_{40}O$, pristanol).

Some fatty alcohols have one double bond (monounsaturated). Their general formula is: $CH_3(CH_2)_x CH=CH(CH_2)_y—CH_2OH$. The unique double bond may be found in different positions: at the C-6: i.e. cis-6-octadecen-1-ol (petroselenyl alcohol), the C-9 i.e, cis-9-octadecen-1-ol (oleyl alcohol) or the C-11 i.e., cis-11-octadecen-1-ol (vaccenyl alcohol).

Some alcohols have isoprenoid structures, such as Geraniol, Farnesol, Geranylgeraniol, Solanesol, or Castaprenols-Ficaprenols. These isoprenoid alcohols are also known as terpenols or polyprenols. They are important molecules in the synthesis of various terpenes, the acylation of proteins and the synthesis of vitamins (Vitamins E and K). Geraniol (from rose oil), is a monoterpene (2 isoprene units), farnesol (present in small amounts in essential oils) is a sesquiterpene (3 isoprene units), geranylgeraniol is a diterpene. Mono- and sesquiterpenes can be obtained by steam distillation of the tissues of many plants. One type of polyisoprenoid alcohols with one saturated isoprenoid unit (dolichol) is well known for its important role as glycosyl carrier in the synthesis of polysaccharides in bacteria and animals (similar compounds have the same function in plants).

Di-functional initiators contain two groups or moieties capable of initiating a lactone ring-opening polymerization. Preferred di-functional initiators are $C_4$ or higher compounds possessing two primary aliphatic alcohol groups, such as 1,4-butanediol, 1,5-pentanediol, 1,6-hexanediol, 1,7-heptanediol, 1,8-octanediol, 1,9-nonanediol, 1,10-decanediol, 1,12-dodecanol, 1,16-hexadecanediol, and especially diethylene glycol. The later is an example of a diol containing an extra heteroatom.

It may be necessary to determine the composition of the formed polymers. The use of NMR (nuclear magnetic resonance) in elucidating structure is well known. Because the amounts of initiator are relatively small, it may be difficult to identify what initiators were employed in the polymerization. One convenient way to do so, however, is to completely hydrolyze the polyester concurrently converting the initiator moiety back to the corresponding original free initiator. For example, a p-dioxanone glycolide copolymer initiated with dodecanol and diethylene glycol would have the alcohols converted to esters in the course of the polymerization. Hydrolysis of the polyester would result in the generation of 2-hydroxyethoxyglycolic acid (ring opened form of p-dioxanone), glycolic acid, dodecanol and diethylene glycol. The composition could then be determined by analyzing the hydrolyzate by a suitable means. These include LC (liquid chomatographic) methods.

The polymers of the present invention either crystallize at a faster rate, or crystallize to a higher extent, or both, than their counterparts made with either a monofunctional initiator alone or a di-functional initiator alone. Crystallizing at a higher rate has advantages when melt processing the polymers of the present invention. This is especially true when fabricating, e.g. medical devices, using an injection molding process. Rapid crystallization is particularly advantageous when injecting molding articles from resins with low glass transition temperatures, because dimensional stability is usually achieved by crystallization. In the absence of crystallization, injection molded parts made from polymers possessing low glass transition temperatures also frequently display distortion and deformation upon removal from the mold because they are not able to withstand the forces exerted, however mild, during the removal process. As articles crystallize faster, cycle times may be decreased. Not only is there potential for an economic impact, i.e., decreased costs, faster cycle times reduce the time the polymer resides in the machine at elevated temperatures. This reduces the amount of degradation that may occur, further improving part quality. The amount of crystallinity needed in the part prior to ejection from the mold depends on glass transition temperature of the resin as well as the molecular weight of the resin. The lower the glass transition temperature, the higher the level of crystallinity required. It is advantageous to have a crystallinity level of at least 10% with some synthetic absorbable polymers possessing low glass transition temperatures. In the case of fibers, with higher molecular orientation, the level of crystallinity required is higher. In such cases, at least about 15% and desirably greater than about 25% may be necessary to provide dimensional stability.

Achieving higher levels of crystallinity may also be advantageous, in that articles manufactured from the polymers, e.g. medical devices, may exhibit better dimensional stability, higher strength and stiffness. Increasing nucleation rates provide many more sites for the initiation of crystal formation. This in turn increases the number of crystals. With more crystals forming in a given volume, it is easy to see that each crystal must necessarily be smaller in size, once crystallization is finished. Smaller crystal size can result in a much tougher material. It has often been observed that the polymer morphologies of the polymers of the present invention that are developed during crystallization from the melt are much finer-grained than polymers made with either a monofunctional initiator alone, or a di-functional initiator alone. The smaller crystal size has positive impact on certain physical characteristics. For instance, in the case of injection molded suture clips, a tough absorbable resin with a glass transition below room temperature would allow a one-piece, hinged, clip design. The high stress on the hinge that is developed during closure when the clip is in place and activated, however, can limit the use of the clip. Having a finer grain (smaller crystal size) allows the clip to withstand higher loads for longer time. Such clips are exemplified in U.S. Pat. Nos. 5,409,499 and 5,234,449, the contents each of which are hereby incorporated by reference in their entirety.

In the case of undyed 92/8 (mole %) PDO/GLY segmented block copolymers, crystal sizes commonly run in the 50 to 100 micron range. It is often advantageous to have finer grained molded articles to provide, for instance, superior toughness. When employing the polymerization processes of the subject invention, an average crystal size (diameter) of less than 10 microns was experimentally observed. Desirably, average crystal size of the inventive copolymer is about 25 microns or less. Crystal sizes of the copolymer were measured in accordance with teachings described herein. In cases where the inventive copolymers have been subjected to various fabrication techniques, for example molding into a device or finished product, it may be necessary to first isolate the polymer in order to analyze the crystal size.

In order to explore the effect of using combinations of monofunctional and di-functional initiators on crystallization properties of undyed polylactone copolymers and medical devices made therefrom, supramolecular crystalline morphology and crystallization kinetics of polylactone copolymers prepared according to processes of the present invention were evaluated utilizing Hot Stage Optical Microscopy (HSOM) and Differential Scanning Calorimetry (DSC), using both isothermal and non-isothermal conditions. The development of spherulites, both in terms of nucleation and growth, can be accurately described by optical measurements, whereas calorimetric data more precisely reflect the overall rate of crystallization. One of the big advantages of HSOM is that nucleation and spherulitic growth rates in, for example, PDO/glycolide segmented block copolymers, can be determined separately; de-convoluting the crystallization process into the two parts. With these two complementary techniques, the entire scope of the crystallization process can be examined.

Calorimetric results were generated on a TA Instruments Differential Scanning Calorimeter, Model 2910 MDSC, using dry $N_2$ as a purge gas. Both non-isothermal and isothermal crystallization studies were conducted. In non-isothermal conditions, after melting of the polylactone copolymer, the copolymer was cooled under a controlled rate; or, after melting, the copolymer was quenched below its glass transition temperature, then heated under a controlled rate. In the isothermal studies, after melting the copolymer, the melted copolymer was cooled rapidly to a temperature of interest and the crystallization measured under those isothermal conditions.

In a typical non-isothermal crystallization of polylactone copolymers utilizing a constant cooling rate, a polymer sample weighing around 4 mg first was heated to approximately 35–40° C. above its melting temperature and held in the molten state for five minutes to eliminate any crystallinity in the polymer. A subsequent cooling step was performed at a constant rate, q, and the crystallization exotherm recorded. In a non-isothermal crystallization run utilizing a constant heating rate, the polymer sample first was heated to approximately 35–40° C. above its melting point and then quenched from its amorphous, melted state to below its glass transition temperature, followed by a controlled heating step.

In an isothermal crystallization of polylactone copolymers, a polymer sample of about 4 mg first was heated to a temperature about 35–40° C. above its melting point and maintained as a melt for five minutes in order to remove any vestiges of the nucleation sites originally present in a sample. Subsequently, the melted polymer was cooled rapidly, e.g. at a rate of 35° C./min, to the constant test (crystallization) temperature. The isothermal method assumes that no crystallization occurs before the sample reaches the test temperature. Crystallization behavior was characterized over a wide range of temperatures, e.g. between 20° C. and 80° C. The isothermal heat flow curve then was integrated to determine the crystallinity as a function of time. The evolution of crystallinity with time can be assessed from the degree of crystallization, $\alpha$, which is expressed by the ratio:

$$\alpha = \frac{\Delta H_t}{\Delta H_\infty} = \frac{\int_0^t \frac{dQ}{dt} dt}{\int_0^\infty \frac{dQ}{dt} dt} \tag{1}$$

where $dQ/dt$ is the respective heat flow, $\Delta H_t$ is the partial area between the DSC curve and the time axis at time t, while $\Delta H_\infty$ is the total area under the peak and corresponds to the overall heat of crystallization. The degree of crystallization, $\alpha$, is the crystalline volume fraction developed at time t.

Dimensional stability of an article can be readily determined. In the case of injection molded articles, dimensional comparison to the mold can be made to ascertain warpage. Dimensional stability of parts is important during shipping and storage where the part may be exposed to slightly elevated temperature, again causing warpage or shrinkage of certain key dimensions. The driving force to warp, distort or shrink is related to the amount of molecular orientation (stress) generated during the molding process. The greater the amount of orientation, the greater the drive to distort as temperatures are raised. Assessment of dimensional stability can be done by subjecting test samples to increasing temperature, followed by measuring and recording dimensional changes. The resulting profile provides a useful characterization.

HSOM was conducted using a Mettler FP90 central processor with a Mettler FP82HT hot stage to control sample conditions. The hot stage, with nitrogen flow, was mounted on a Nikon SMZ-U microscope equipped with a 1× objective and a 1:10 zoom. Images from the microscope were obtained using a Microimage i308 Low Light Integrating Video Camera. The digital images were captured and analyzed using Image Pro Plus (Version 4.0) imaging software.

Growth rate measurements at each temperature were conducted on freshly prepared polymer films to avoid possible degradation issues that might arise with these hydrolytically unstable polylactone polymers. The polymer film samples were prepared in the following manner. A small amount of ground polymer was placed on the microscope glass slide and a thin cover glass positioned on top of it. The resulting sandwich then was inserted into a hot stage block regulated at, or above, the equilibrium melting point, to render the sample molten. In the case of the polymers of Example 1 (Polymers 1A to 1E), this temperature was 140° C. The polymeric sample then was heated for two minutes under a nitrogen purge to melt. A thin film was obtained by applying slight pressure on the top of the cover glass. Monitoring with a digital micrometer, the polymer film thickness was adjusted to 0.135 mm for each sample run. The thin film samples were then melted for an additional five minutes at, or above, the equilibrium melting temperature (140° C. in the case of the polymers of Example 1) in a separate hot stage apparatus as described above. They were then quickly brought to a second pre-heated measuring device to perform isothermal measurements.

Some supporting evidence was obtained by conventional Wide Angle X-Ray Diffraction (WAXD) analysis. The WAXD measurements of the isothermally grown films were carried out on a Siemens Hi-Star™ unit using CuKα radiation at the wavelength of 1.542 Å. The instrument was operated at 40 kV and 40 mA with the collimator size of Ø 0.5 mm. The convolution of the X-ray images and the calculation of crystallinity content were conducted using the DIFFRAC PLUS™ software developed by Siemens.

EXAMPLE 1

A series of undyed 92/8 (mole %) PDO/GLY segmented block copolymers were prepared by ring-opening polymerization in a metal reactor outfitted with a suitable agitator, as described below, using stannous octoate as a monomer-to-catalyst mole ratio of 30,000:1, utilizing various ratios of mono-functional initiator, e.g. dodecanol (DD), to di-functional initiator, e.g. diethylene glycol (DEG), (See table 1).

The polymerization process used in preparation of the PDO/GLY block copolymer 1C is a two stage block co-polymerization comprising a first stage homopolymerization using 100% p-dioxanone and a second stage block co-polymerization with an added monomer composition of 100 mole % glycolide. The overall final composition provides a polymer comprising 92 mole % polymerized p-dioxanone and 8 mole % polymerized glycolide. The catalyst and initiators are added with the first stage monomer. The overall monomer to catalyst ratio is 30,000 moles of monomer per mole of catalyst. The monomer to catalyst ratio based on first stage monomer and the quantity of catalyst added is 27,600 moles of monomer per mole of catalyst. The monomer to initiators ratio for this example is 1,000 to 1. Thus for this 50/50 mole % mixture of DD and DEG as the initiators, the monomer to DD ratio is 2,000 to 1 and the monomer to DEG ratio is 2,000 to 1.

In the first stage, 10.26 kilo-grams p-dioxanone, 10.18 grams DD, 5.8 grams DEG and 11.0 ml of a 12.6 w/v % stannous octoate catalyst solution were charged under a nitrogen purge to a clean, dry stainless steel, oil-heated, jacketed reactor equipped with a mechanical agitator. The vessel was evacuated to less than 1,000 mTorr for about 20 minutes, after which nitrogen gas was introduced to raise the pressure slightly over atmospheric (approximately +5 psi). The evacuation/nitrogen purge process was repeated using a 25-minute vacuum-hold period. The constituents were heated under constant agitation to 110° C. and then maintained at this temperature for about four and one-half hours. The temperature of the oil entering the outer jacket of the reactor was increased to 135° C. The second-stage monomer (1,014 grams glycolide) was then added under nitrogen purge. Glycolide can be added as a solid or in melted form, although the later is frequently preferred. The stirrer speed was increased to 20 RPM for the first 15 minutes of the second-stage to enhance blending of ingredients. The polymerization was continued for three and one-half hours. The polymer was discharged into trays. When the polymer was cool to the touch, the polymer was placed into tared storage bags, weighed and transferred to freezer storage. The frozen polymer was subsequently ground and sieved—size reduction and classification—and dried under vacuum at elevated temperature.

The dried polymer 1C had the following properties:

Inherent Viscosity 1.61 dL/g, as determined at 25.0° C. in hexafluroisopropanol (HFIP) at a concentration of 0.1 g/dL
Melt Index 0.120 g/10 minutes (150° C., 6,600 gram weight, 0.026" diameter die opening with a 0.315" die length) using a Tinius Olsen Extrusion Plastometer
Mw 68,000 g/mole
Mn 24,000 g/mole
Composition: mole %, by NMR: Polymerized PDO 91.6, Residual PDO 0.3, Polymerized GLY 8.1, Residual GLY 0.0.

The dried polymer was stored under vacuum until ready for use or evaluation.

Crystallization characteristics of polymers and films made therefrom were evaluated.

TABLE 1

| Polymer ID | DD/DEG molar ratio (%) | Monomer to initiators ratio | IV ((dL/g) | $M_w$ (g/mol) |
|---|---|---|---|---|
| 1A | 100/0 | ~1,200:1 | 1.73 | 80,000 |
| 1B | 75/25 | ~1,000:1 | 1.77 | 73,000 |
| 1C | 50/50 | ~1,000:1 | 1.61 | 68,000 |
| 1D | 25/75 | ~1,000:1 | 1.55 | 55,000 |
| 1E | 0/100 | ~800:1 | 1.41 | 49,000 |

EXAMPLE 2

A series of five 150 gram undyed 95/5 (mole % L(−) lactide/glycolide) random copolymers were prepared by ring-opening polymerization in a round bottom glass reactors outfitted with a suitable agitator, using stannous octoate at a monomer-to-catalyst mole ratio of 160,000:1 and utilizing various ratios of mono-functional initiator, e.g. dodecanol (DD), to di-functional initiator, e.g. diethylene glycol (DEG). See Table 2. Crystallization characteristics of polymers and films made therefrom were evaluated.

TABLE 2

95 m % L(−)LAC - 5 m % GLY Random Copolymers

| Polymer ID | DD/DEG molar ratio (%) | Monomer to initiators ratio | IV (dL/g) | $M_w$ (g/mol) |
|---|---|---|---|---|
| 2A | 100/0 | ~570:1 | 1.72 | 110,000 |
| 2B | 75/25 | ~570:1 | 1.72 | 110,000 |
| 2C | 50/50 | ~570:1 | 1.64 | 102,000 |
| 2D | 25/75 | ~570:1 | 1.60 | 98,000 |
| 2E | 0/100 | ~570:1 | 1.52 | 92,000 |

Crystallization kinetics during spherulite growth are usually expressed via radius or diameter growth rates, dR/dt or dD/dt, where t is the time and R (D) the radius (diameter) of the spherulite, measured by means of an optical micrometer. The general expression of crystal growth is described by Lauritzen and Hoffman as:

$$G = \frac{dR}{dt} = G_0 \exp\left(-\frac{U^*}{R_0(T_C - T_\infty)}\right) \exp\left(-\frac{K_g}{T_C \Delta T f}\right) \quad (2)h$$

where G is the growth rate dR/dt, $G_0$ is the growth rate constant, $U^*$ represents the activation energy for polymer diffusion, $R_0$ the gas constant and $T_C$ the crystallization temperature. $T_\infty$ is the temperature at which molecular motion is frozen and viscosity approaches an infinitive value. Hoffman et. al. suggest using a value for $U^*$ of 1500 cal/mol and that $T_\infty$ can be approximated by $T_g$−30, where $T_g$ is the glass transition temperature of the polymer ($T_g$=−7° C. for the 92/8 PDO/GLY copolymers). The term $\Delta T$ in Equation 2 stands for the amount of undercooling ($\Delta T = T_m° - T_C$), where $T_m°$ is the equilibrium melting temperature ($T_m° = 140°$ C. for the 92/8 PDO/GLY copolymers and for PDS, as found by optical microscopy). Parameter f is a dimensionless term expressed by $f = 2T_C/(T_C + T_m°)$. $K_g$ is the nucleation rate constant.

Figure 1:
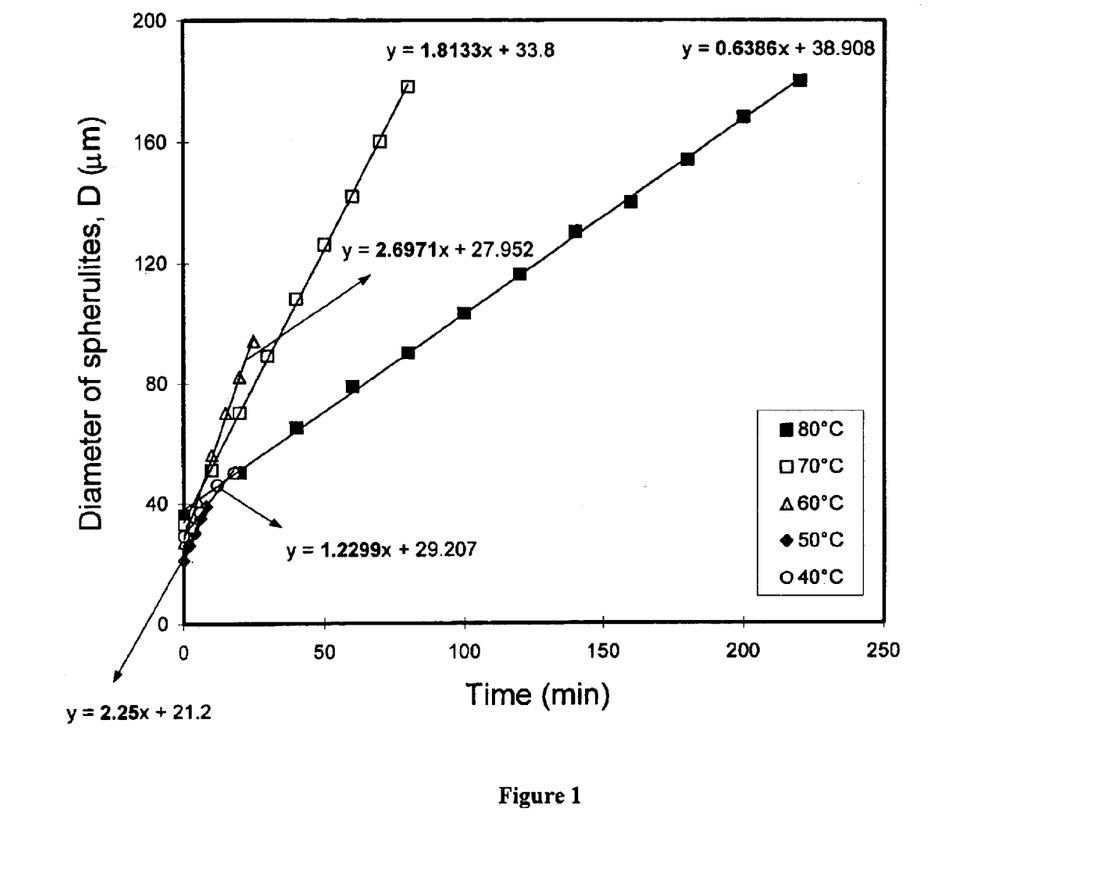
FIG. 1 is a series of plots at various crystallization temperatures of spherulite diameter versus time for the isothermal crystallization of copolymer 1D.

As shown in FIG. 1, the spherulite diameter was plotted against time for polymer 1D crystallized at various constant temperatures. These data clearly show that the radius of the supramolecular formations grew linearly with time over the entire range of investigated crystallization temperatures. The average linear correlation coefficient found in these plots suggests almost a perfect linearity, implying that the growth rates were independent of the size of the spherulites. The slopes of the curves generated (see FIG. 2) were a smooth function of the crystallization temperature, in that dD/dt systematically increased to a maximum value, then decreased as the melting point was approached. Radial growth ceased only when all surfaces were bounded or impinged.

In order to correlate data that were obtained during various spherulitic growth measurements with the Lauritzen-Hoffman theory, Equation 2 can be rewritten in the following form:

$$\ln G + \frac{U^*}{R_0(T_C - T_\infty)} = \ln G_0 - \frac{K_g}{f T_C \Delta T} \quad (3)$$

A linear plot can be obtained by drawing the left-hand side of Equation 3 as a function of $1/fT_C\Delta T$. The intercept of this plot is ln $G_0$ and its slope is the nucleation constant $K_g$. The growth rates G were determined earlier from the slopes of the lines displayed in FIG. 1.

Figure 2:
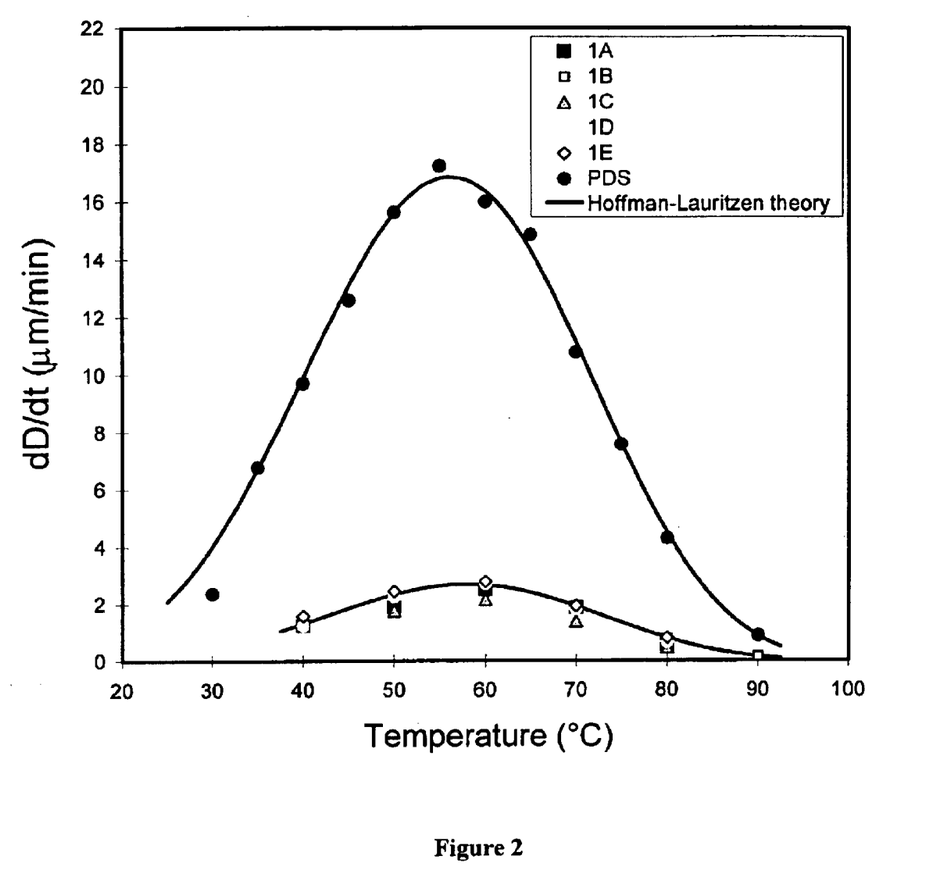
FIG. 2 is a plot of experimentally-obtained spherulitic growth rates, dD/dt (micron/min), obtained at various isothermal crystallization temperatures for copolymers 1A–1E and PDS homopolymer and the expected relationship based on the Hoffman-Lauritzen theory (See Hoffman, J. D, Davis, G. T, Lauritzen, J. I. 1976, Treatise on Solid State Chemistry, Hannay N B, editor, Plenum Press: New York, Chapter 7.).
Figure 3:
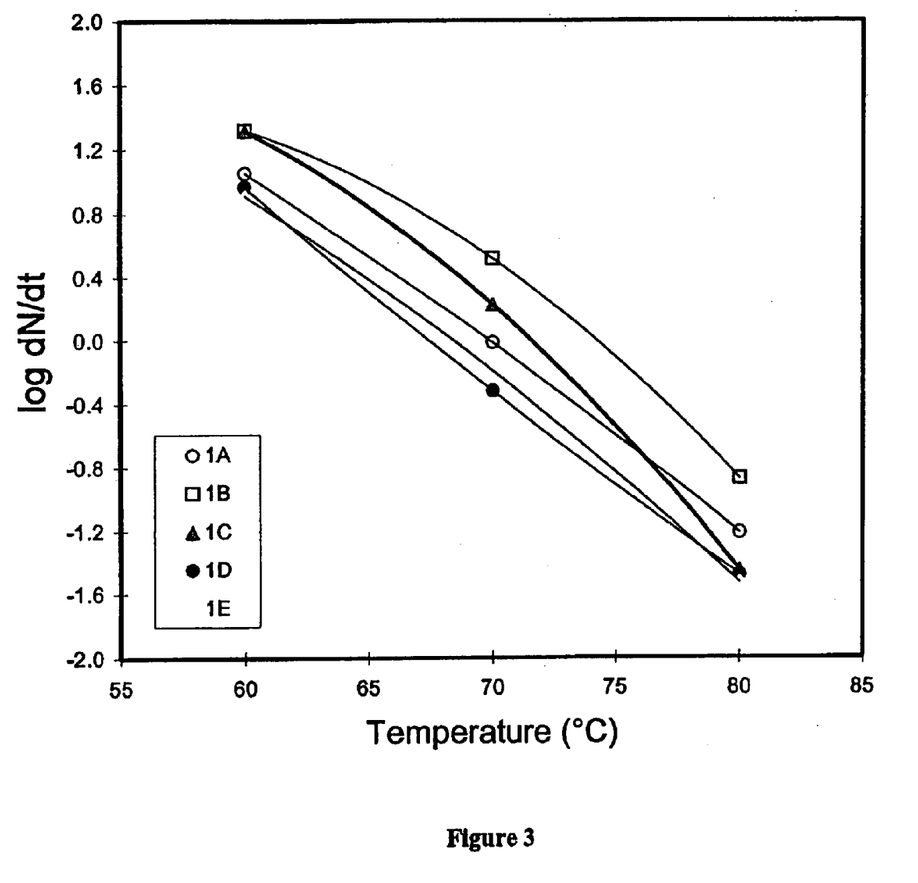
FIG. 3 is a semi-logarithmic plot of nucleation rates (dN/dt) versus crystallization temperature for copolymers 1A–1E.

Experimentally determined growth rates, G=dD/dt, are plotted against temperature in FIG. 2 for the series of copolymers of Example 1 and a PDS homopolymer as a comparison. Results showed a characteristic "bell-shaped" dependence between crystal growth rate and crystallization temperature, with the maximum rate observed at intermediate temperature zones. Data clearly indicates that for any given crystallization temperature, the spherulitic growth rate of PDS homopolymer is significantly higher (~8×) than those obtained from the copolymer series of Example 1. The reason for this behavior can be attributed to the disruptive role that glycolic acid comonomer plays in the overall ability of the copolymer's macromolecular chains to align properly for the crystal formation. In the series of copolymers of Example 1, there is practically no difference in the crystallization kinetics for the temperature range used except for sample 1C, which crystal growth was found slightly slower than those of the other copolymers in the series. Solid lines that connect data points of PDS and polymers of Example 1 were calculated according to Equation 2, using the previously obtained values for $K_g$ and ln $G_0$ from FIG. 3. The excellent fit of the model (note that no adjustable parameters are involved) over a very broad range of temperatures is particularly noted.

The second part of an isothermal supramolecular crystallization analysis involves the nucleation density evaluation. Nucleation density, the number of nuclei per unit volume, generally increases with increasing molecular weight, but decreases with increasing crystallization temperature. An estimation of the nucleation rate using HSOM usually requires a manual counting of nucleation sites present in an arbitrary chosen field of the sample as a function of time. In order to determine nucleation rates, the initial slopes of these curves were calculated as a function of crystallization temperatures. Such obtained nucleation rates, dN/dt, are plotted in FIG. 3 over a limited temperature range. These data suggest that, within the experimentally accessible region, i.e. 60° to 80° C., polymer 1B exhibits the highest nucleation rates.

Figure 4:
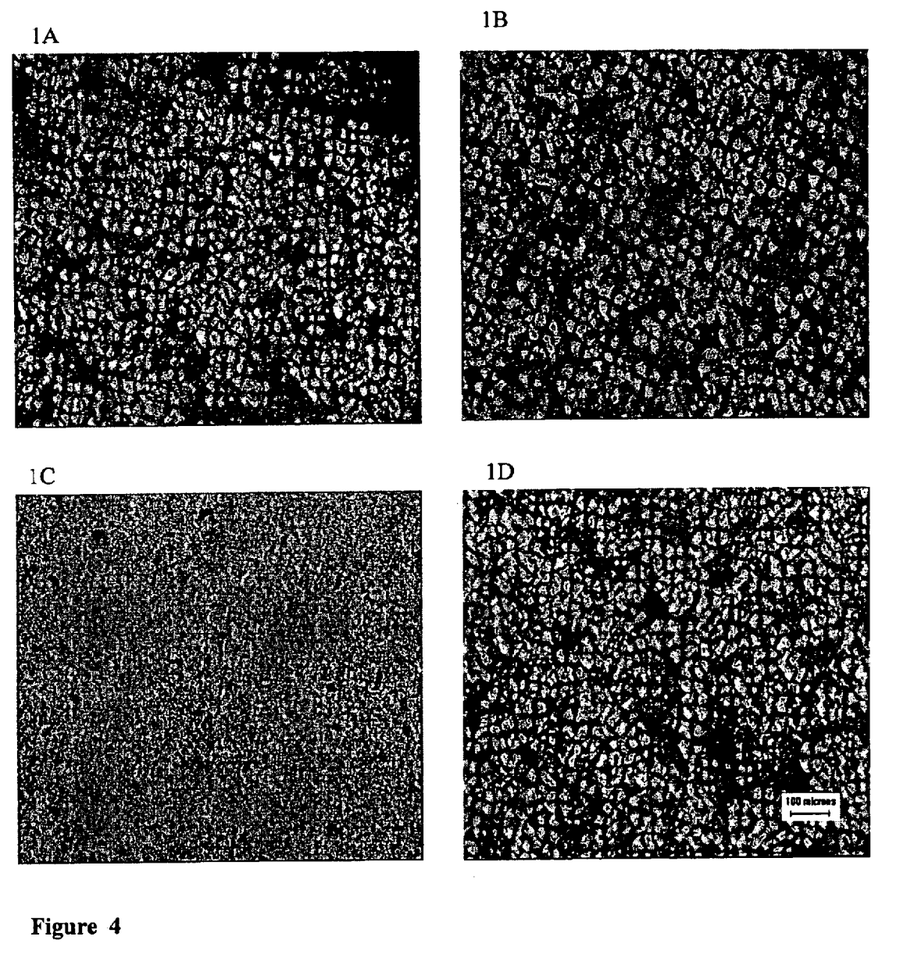
FIG. 4 shows Hot Stage Optical Microscopy images of copolymers 1A–1D, captured after 60 minutes of isothermal crystallization at 40° C.

Outstanding crystallization properties of polymer 1C were discovered when studied under those conditions. First, the nucleation rates for copolymer 1C, observed at higher temperatures, were found slower than in polymer 1B, but increased rather abruptly when the crystallization temperature is lowered (see FIG. 3). When studied at a lower temperature range, a visual inspection of the copolymer's crystalline morphology indicated that, due to the extensive nucleation process, total crystal impingement occurred almost instantaneously (see FIG. 4). It was discovered that the nucleation density of polymer 1C was extremely high compared to the balance of copolymers described in Table 1. While not intending to be bound by this theory, such a high degree of nucleation apparently controlled the crystal growth via an impingement process, even at very early stages of the process. Thus, the boundaries of developed structures approached each other, causing the crystals to stop growing. This produced, in turn, a large number of crystals with very small size. It was estimated that the average diameter of the crystals at the studied conditions (40° C. after 60 minutes) was about 8 microns. The balance of the copolymers described in Table 1 had a value significantly higher at about 70 microns.

The overall crystallization rates depend heavily on two factors: the concentration of growing spherulites with time (nucleation rate) and the rate of spherulite growth. It is anticipated that these processes would have a measurable effect on calorimetric data. DSC has several technical advantages including small sample size, an easy-to-handle apparatus, and more importantly, the ability to achieve a rapid thermal equilibrium, especially at high undercooling. Because of these characteristics, DSC has been one of the most convenient and popular methods in studying crystallization behavior of polymers using both, non-isothermal and isothermal methods.

Figure 5:
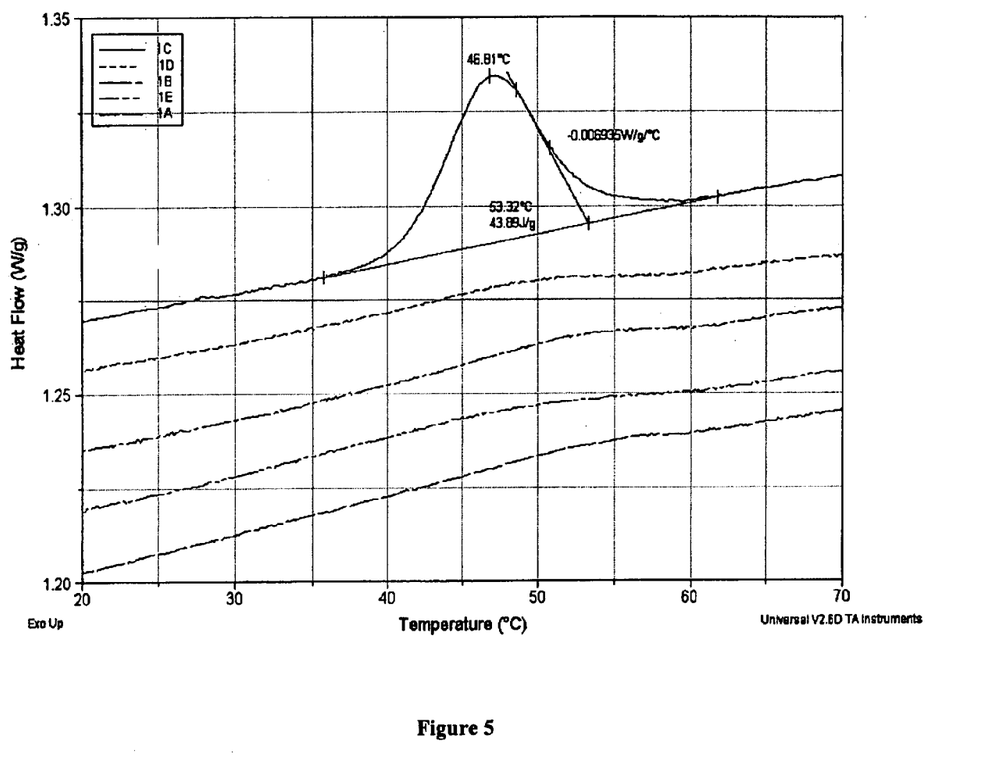
FIG. 5 is a non-isothermal DSC trace, including a slope value, obtained during crystallization from the melt at a constant cooling rate of 0.5° C./minute of copolymer 1C.

DSC data generated on the copolymers of Example 1 during cooling from the melt support earlier evidence from HSOM, indicating clearly superb crystallization behavior of copolymer 1C. A thermogram captured during the constant cooling rate (0.5° C./min) experiment for this copolymer is shown in FIG. 5. Several important parameters can be extracted from this figure. The high temperature slope of the peak represents the crystallization rate under given conditions. The area under the peak is proportional to overall crystallinity in the material. The temperature at the maximum peak indicates the location of the crystallization processes at the given cooling rate. A summary of thermal characteristics for all the copolymers of Example 1 and a PDS homopolymer obtained by the same method is listed in Table 3.

TABLE 3

Non-isothermal crystallization data obtained during the constant cooling rate of 0.5° C./min for a series of VLM copolymers and a PDS homopolymer.

| Polymer | $T_C$ (° C.) | Peak area at $T_C$ (J/g) | $\alpha$ (%)* | Absolute Value of Slope** ($Wg^{-1}$ ° $C.^{-1}$) | Relative Rate*** |
|---|---|---|---|---|---|
| Copolymer 1 A | 52.5 | 8.2 | 6.7 | 0.000265 | 0.9X |
| Copolymer 1 B | 52.1 | 8.9 | 7.2 | 0.000219 | 0.8X |
| Copolymer 1 C | 46.8 | 43.9 | 35.3 | 0.00694 | 24.7X |
| Copolymer 1 D | 48.5 | 9.3 | 7.5 | 0.000154 | 0.5X |
| Copolymer 1 E | 48.7 | 10.2 | 8.2 | 0.000298 | 1.1X |
| PDS Homopolymer | 57.8 | 39.3 | 31.7 | 0.00381 | 13.5X |

*A measure of the crystallinity level, based on a heat of fusion value for 100% crystalline material of 124 J/g.
**A measure of the rate of crystallization.
***Rate relative to the average of the rate observed for copolymer made with pure mono-functional initiator and for copolymer made with pure di-functional initiator.

For this set of conditions, copolymer 1C crystallized radically faster, e.g. 25×, and to a much higher extent, e.g. 4–5× than the rest of the copolymers of Example 1. In addition, about a 2–6° C. lower crystallization temperature observed for polymer 1C suggests that, in this particular case, the extensive nucleation at lower temperatures is the most dominant crystallization mechanism. It was unexpectedly discovered that both the crystallizability and non-isothermal kinetics of this material are even greater than those calculated for the PDS homopolymer alone. A comparison of DSC crystallization data between copolymer 1C and PDS homopolymer obtained using a wide range of cooling rates revealed the same trend. Copolymer 1C showed faster crystallization and a higher overall crystallinity than the PDS homopolymer and the balance of the copolymers of Example 1.

The second part of the non-isothermal DSC crystallization study was conducted on the copolymers of Example 1 utilizing controlled heating steps. Samples were initially quenched from the molten state to obtain a fully amorphous morphology and subsequently heated at rates of 2.5, 5.0, 7.5 and 10° C./min, respectively.

DSC thermograms suggested that the area under the crystallization peaks equals roughly that for a fusion process, suggesting that the heating scan started from the fully amorphous samples. For the copolymers of Example 1 tested, at the constant hearing rate of 10° C./min, the $T_g$s of the copolymers in semi-crystalline and amorphous states were −3° C. and −7° C., respectively. At the same heating rate employed, the unannealed material melts at approximately 90° C. (about 8° C. lower than PDS). For all Example 1 copolymers studied, the melting point locations obtained after the first (annealed) and second (unannealed) heating runs, as well as the heat of fusion generated on the annealed samples, were found almost constant for the test conditions used. On the other hand, due to the significantly higher crystallization tare, the melting peak area (corresponding to the crystallinity level) of copolymer 1C was larger than that of the balance of the copolymers of Example 1. In addition, at the given heating rate used, the copolymer crystallized to considerably higher extent than the PDS homopolymer. This unusual finding, obtained under non-isothermal heating conditions, is in line with the relative crystallization rates observed earlier for the samples crystallized under non-isothermal controlled cooling rate experiments.

The kinetic data for isothermal melt crystallization of copolymer 1C were analyzed using a classical Avrami approach. According to the Avrami model, the time dependence of $\alpha$ can be described by the following kinetic expression:

$$-ln(1-\alpha) = K \times t^n \qquad (4)$$

where K is the composite rate constant and n is the Avrami exponent, typically ranging from 2 to 4 for semicrystalline polymers. These constants are related to the crystallization half-time, $t_{1/2}$, and to the type of nucleation and geometry of the crystal growth. Crystallization half-time, $t_{1/2}$, is the time needed for crystallinity to reach 50% conversion. The Avrami exponent, n, was determined from the slope of the $log[-ln(1-\alpha)]$ vs. log t curve. Finally, the composite rate constant, K, can be evaluated either from the intercept or calculated using the following expression:

$$K = \frac{\ln 2}{t_{1/2}^n} \qquad (5)$$

The value $t_{1/2}$ was determined by fitting each set of data to Equation 4 and then graphically locating the crystallization time that corresponds to $\alpha=0.5$. Using this approach, it was found that an excellent agreement exists between the actual experimental data and theory. A summary of important kinetic parameters is listed in Table 4 for the temperature range between 35 to 60 C. A data comparison with PDS homopolymer is given in the table as well.

TABLE 4

Isothermal crystallization data for Copolymer 1C and PDS homopolymer.

| Polymer | T (° C.) | $T_{1/2}$(s) | N | K ($t^{-n}$) | $\Delta H_c$ (J/g) | $\alpha$ (%)* |
|---|---|---|---|---|---|---|
| 1C | 35 | 1140 | 2.60 | 7.81e−9 | 42.1 | 34.0 |
|  | 40 | 930 | 2.60 | 1.42e−8 | 41.2 | 33.2 |
|  | 45 | 1000 | 2.59 | 1.10e−8 | 41.1 | 33.2 |
|  | 50 | 1110 | 2.85 | 1.49e−9 | 44.0 | 35.5 |
|  | 60 | ~2500 | / | / | / | / |
| PDS Homo- | 35 | 570 | 2.57 | 5.73e−8 | 32.0 | 25.8 |
|  | 40 | 525 | 2.51 | 1.03e−7 | 31.3 | 25.2 |

TABLE 4-continued

Isothermal crystallization data for Copolymer 1C and PDS homopolymer.

| Polymer | T (° C.) | T½(s) | N | K (t$^{-n}$) | ΔH$_c$ (J/g) | α (%)* |
|---|---|---|---|---|---|---|
| polymer | 45 | 400 | 2.41 | 3.71e−7 | 31.2 | 25.2 |
|  | 50 | 470 | 2.42 | 2.37e−7 | 31.4 | 25.3 |
|  | 60 | 800 | 2.53 | 3.24e−8 | 39.5 | 31.8 |

*A measure of the crystallinity level, based on a heat of fusion value for 100% crystalline material of 124 J/g.

The analysis of the half-time values indicates that they are a strong function of T$_c$. The fastest isothermal crystallization rate (the lowest t$_{1/2}$ value) for copolymer 1C was detected at 40° C. This temperature is lower than that that of the homopolymer (45° C.), because of the extensive nucleation mechanism observed for the copolymer at lower temperatures. Despite significantly higher nucleation rates, overall crystallization rates for the copolymer were found slower for all studied isothermal conditions. Overall crystallization rates do not exactly follow the nucleation trends observed earlier by HSOM measurements, because the second part of the crystallization process for PDS homopolymer, i.e. spherulitic growth, is more than eight (8) times faster at any given temperature (see FIG. 2). However, a copolymer's nucleation effect on overall isothermal crystallization is still very pronounced. The overall crystallization rate (t$_{1/2}$ values in Table 4) is only about half that of the PDS homopolymer.

Geometry of the crystal habit during isothermal crystallization of copolymer 1C, expressed via the Avrami exponent, n, is also listed in Table 4. The values of n were relatively constant at 2.6 indicating that the crystal growth was three-dimensional. A nearly identical value was found earlier for the PDS homopolymer (2.5).

Finally, data from Table 4 suggest that crystallization content of isothermally treated copolymer 1C was significantly higher than in the PDS homopolymer at any given crystallization temperature. This is also in agreement with results obtained during non-isothermal crystallization measurements utilizing controlled heating and cooling rates. The percent of crystallinity determined from DSC heat of fusion were additionally confirmed by the WAXD technique. A big advantage of the copolymers having higher crystal content is the boost in mechanical properties, which in turn, can improve functioning of many current and future products based on these absorbable materials.

What is claimed is:

1. An absorbable polylactone copolymer, comprising:
   from about 5 mole percent to about 10 mole percent of a first polymerized lactone comprising polymerized glycolide and about 95 mole percent to about 90 mole percent of a second polymerized lactone other than polymerized glycolide, wherein said copolymer has a degree of crystallinity of at least about 15%.

2. The copolymer of claim 1, wherein said second polylactone is prepared from lactone monomers selected from the group consisting of p-dioxanone, lactide, ε-caprolactone and trimethylene carbonate and combinations thereof.

3. The copolymer of claim 1, comprising about 8 mole percent polymerized glycolide and about 92 mole percent polymerized p-dioxanone, said copolymer having a degree of crystallinity of from about 20 to about 40%.

4. A medical device, comprising:
   an absorbable polylactone copolymer, said copolymer comprising from about 5 mole percent to about 10 mole percent of a first polymerized lactone comprising polymerized glycolide and about 95 mole percent to about 90 mole percent of a second polymerized lactone other than polymerized glycolide, wherein said copolymer has a degree of crystallinity of at least about 15%.

5. The device of claim 4 wherein said second polylactone is prepared from lactone mononers selected from the group consisting of p-dioxanone, lactide, ε-caprolactone and trimethylene carbonate.

6. The device of claim 4 wherein the copolymer comprises about 8 mole percent polymerized glycolide and about 92 mole percent of polymerized p-dioxanone, said copolymer having a degree of crystallinity of from about 20 to about 40%.

7. The medical device of claim 4 selected from the group consisting of sutures, clips, staples and fibers.

8. The medical device of claim 4 which is capable of being deformed.

9. The medical device of claim 4 which is repeatedly deformable.

10. The medical device of claim 4 which is resiliently deformable.

11. A composition for producing an absorbable polylactone copolymer comprising:
   a.) about 2 mole percent to about 80 mole percent a first lactone monomer comprising glycolide;
   b.) from about 98 to about 20 mole percent of a second lactone monomer other than glycolide;
   c.) a monofunctional initiator; and
   d.) a di-functional initiator;
   wherein the molar ratio of mono-functional to di-functional initiator is from about 10:90 to about 90:10.

12. The reaction product of the composition of claim 11.

13. The reaction product of claim 12 having a degree of crystallinity at least 15% using non-isothermal crystallization under a substantially constant cooling rate of about 0.5° C./minute.

14. An absorbable polylactone copolymer comprising from about 5 mole percent to about 10 mole percent of a first polylactone comprising polyglycolide and about 95 mole percent to about 90 mole percent of a second polylactone other than polyglycolide, wherein said copolymer has an average crystal size of about 25 microns or less.

* * * * *